US007867484B2

(12) United States Patent
Samulski et al.

(10) Patent No.: US 7,867,484 B2
(45) Date of Patent: Jan. 11, 2011

(54) HEPARIN AND HEPARAN SULFATE BINDING CHIMERIC VECTORS

(75) Inventors: Richard Jude Samulski, Chapel Hill, NC (US); Zhijian Wu, Chapel Hill, NC (US); Aravind Asokan, Chapel Hill, NC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 58 days.

(21) Appl. No.: 11/698,505

(22) Filed: Jan. 26, 2007

(65) Prior Publication Data

US 2007/0196338 A1 Aug. 23, 2007

Related U.S. Application Data

(60) Provisional application No. 60/762,774, filed on Jan. 27, 2006.

(51) Int. Cl.
*C12N 15/00* (2006.01)
*C12N 15/85* (2006.01)
*C12N 15/86* (2006.01)
*C12N 15/64* (2006.01)

(52) U.S. Cl. ............... 424/93.2; 435/320.1; 435/252.3; 435/325; 435/455; 435/456; 435/471; 536/23.1

(58) Field of Classification Search ............... 424/93.2; 435/320.1, 252.3, 325, 455, 456, 471; 536/23.1
See application file for complete search history.

(56) References Cited

U.S. PATENT DOCUMENTS

| 6,410,300 | B1 | 6/2002 | Samulski et al. | |
|---|---|---|---|---|
| 6,491,907 | B1 | 12/2002 | Rabinowitz et al. | |
| 6,703,237 | B2 * | 3/2004 | Samulski et al. | 435/320.1 |
| 7,172,893 | B2 | 2/2007 | Rabinowitz et al. | |
| 2003/0022870 | A1 * | 1/2003 | Dzau et al. | 514/152 |
| 2006/0188483 | A1 | 8/2006 | Rabinowitz et al. | |
| 2006/0188484 | A1 | 8/2006 | Rabinowitz et al. | |

FOREIGN PATENT DOCUMENTS

WO    WO 00/28004 A1    5/2000

WO    WO 2005/106046 A1    11/2005

OTHER PUBLICATIONS

Rutledge et al. J. Virol. 72;309-319; 1998.*
International Search Report and Written Opinion of International Application No. PCT/US07/02251, mailed Sep. 18, 2008 (13 pages).
Opie et al. "Identification of Amino Acid Residues in the Capsid Proteins of Adeno-Associated Virus Type 2 That Contribute to Heparan Sulfate Proteoglycan Binding" *Journal of Virology* 77(12):6995-7006 (2003).
Wu et al. "Mutational Analysis of the Adeno-Associated Virus Type 2 (AAV2) Capsid Gene and Construction of AAV2 Vectors with Altered Tropism" *Journal of Virology* 74(18):8635-8647 (2000).
Grimm et al. "Helper Virus-Free, Optically Controllable, and Two-Plasmid-Based Production of Adeno-associated Virus Vectors of Serotypes 1 to 6" *Molecular Therapy* 7(6): 839-850 (Jun. 2003).
Grimm et al. "Preclinical in vivo evaluation of pseudotyped adeno-associated virus vectors for liver gene therapy" *Blood* 102(7): 2412-2419 (Oct. 1, 2003).
Halbert et al. "Adeno-Associated Virus Type 6 (AAV6) Vectors Mediate Efficient Transduction of Airway Epithethial Cells in Mouse Lungs Compared to That of AAV2 Vectors" *Journal of Virology* 75(14): 6615-6624 (Jul. 2001).
Jooss et al. "Transduction of Dendritic Cells by DNA Viral Vectors Directs the Immune Response to Transgene Products in Muscle Fibers" *Journal of Virology* 72(5): 4212-4223 (May 1998).
Kern et al. "Identification of a Heparin-Binding Motif on Adeno-Associated Virus Type 2 Capsids" *Journal of Virology* 77(20): 11072-11081 (Oct. 2003).
Vandenberghe et al. "Heparin binding directs activation of T cells against adeno-associated virus serotype 2 capsid" *Nature Medicine*: 1-5 (Jul. 16, 2006).

* cited by examiner

*Primary Examiner*—Maria Leavitt
(74) *Attorney, Agent, or Firm*—Myers Bigel Sibley & Sajovec, P.A.

(57) ABSTRACT

The present invention is based on the finding that parvovirus (including AAV) capsids can be engineered to incorporate small, selective regions from other parvoviruses that confer desirable properties. In some embodiments, a substitution of a single amino acid that is unique to the AAV6 capsid (Lys-531) among other AAVs that have been characterized to date can confer one or more desirable properties to other AAVs.

35 Claims, 5 Drawing Sheets

| Mutant | Parental virus | Mutation (amino acid positions) |
|---|---|---|
| 1 | AAV1 | L129F |
| 2 | AAV1 | E418D |
| 3 | AAV1 | E531K |
| 4 | AAV1 | F584L |
| 5 | AAV1 | A598V |
| 6 | AAV1 | N642H |
| 7 | AAV6 | F129L |
| 8 | AAV6 | D418E |
| 9 | AAV6 | K531E |
| 10 | AAV6 | L584F |
| 11 | AAV6 | V598A |
| 12 | AAV6 | H642N |

Figure 1

US 7,867,484 B2

HEPARIN AND HEPARAN SULFATE BINDING CHIMERIC VECTORS

STATEMENT OF PRIORITY

This application claims the benefit, under 35 U.S.C. §119 (e), of U.S. Provisional Application No. 60/762,774, filed Jan. 27, 2006, the entire contents of which are incorporated by reference herein.

FIELD OF THE INVENTION

The present invention relates to novel viral vectors and methods of purifying and administering the same.

BACKGROUND OF THE INVENTION

Adeno-associated viral (AAV) vectors have been used widely for therapeutic gene transfer to different cell types in vitro and organs in vivo (Grimm et al. (2003) *Curr. Gene Ther.* 3:281-304). The broad tissue tropisms exhibited by different AAV serotypes can be attributed, at least in part, to the distribution of primary and secondary receptors on various cell types (Di Pasquale et al., (2003) *Nat. Med.* 9:1306-12; Kaludov et al., (2001) *J. Virol.* 75:6884-93; Qing et al., (1999) *Nat. Med.* 5:71-7; Summerford et al., (1999) *Nat. Med.* 5:78-82; Summerford et al., (1998) *J. Virol.* 72:1438-45). In this regard, initial cell surface binding of the viral capsid is often mediated through complex cell surface glycosaminoglycans (Grimm et al., (2003) *Curr. Gene. Ther.* 3:281-304). For example, AAV serotype 2 has been shown to utilize heparan sulfate (HS) as a primary receptor for cell attachment (Summerford et al., (1998) *J. Virol.* 72:1438-45). AAV serotypes 4 and 5, which display different tropism with respect to AAV2, utilize sialic acid with different linkage specificities for cell surface binding and transduction (Kaludov et al., (2001) *J. Virol.* 75:6884-93). Similarly, transduction by AAV1, which does not bind heparin, was inhibited by removal of cell surface sialic acid with sialidase (Chen et al., (2005) *Hum. Gene Ther.* 16:235-47). On the other hand, AAV6 which differs from AAV1 by only six amino acid residues (Rutledge et al., (1998) *J. Virol.* 72:309-19) and shares ~85% homology with the AAV2 capsid sequence, binds heparan sulfate and can be purified using heparin-affinity chromatography (Halbert et al., (2001) *J. Virol.* 75:6615-24). It is interesting to note that the AAV6 capsid does not possess the R585 and R588 residues that are primarily responsible for HS binding by AAV2 (Kern et al., (2003) *J. Virol.* 77:11072-81; Opie et al., (2003) *J. Virol.* 77:6995-7006).

Purification schemes for AAV2 based on heparin affinity purification are well defined. Less streamlined are the purification parameters for other serotypes, which do not bind to heparin. It would be desirable to engineer heparin-binding properties into other AAV capsids to provide vectors with universal purification attributes for greater ease of purification. Further, it would be advantageous to transfer AAV capsid sequences conferring desirable characteristics (e.g., tropism) to other AAV capsids to engineer virus vectors with an array of improved properties.

SUMMARY OF THE INVENTION

As one aspect, the invention provides a viral vector comprising an adeno-associated virus (AAV) capsid comprising an amino acid substitution that results in a positively charged amino acid (e.g., lysine, arginine, histidine) at amino acid position 531 in an AAV1 capsid subunit or at the corresponding amino acid position in other AAV capsid subunits.

In further aspects, the present invention provides a virus vector comprising an adeno-associated virus (AAV) capsid comprising an amino acid substitution that results in a cysteine at amino acid position 531 in an AAV1 capsid subunit or at the corresponding amino acid position in other AAV capsid subunits.

In particular embodiments, the virus vector further comprises a recombinant nucleic acid comprising a terminal repeat (TR) sequence and a heterologous nucleic acid sequence; wherein the recombinant nucleic acid is packaged within the AAV capsid.

The invention also provides pharmaceutical formulations comprising a virus vector of the invention in a pharmaceutically acceptable carrier.

As a further aspect, the invention provides a method of delivering a nucleic acid to a cell comprising contacting the cell with a virus vector or pharmaceutical formulation of the invention.

The invention also provides a method of delivering a nucleic acid to a subject comprising administering to the subject a virus vector or pharmaceutical formulation of the invention.

As still another aspect, the invention provides a method of purifying a virus vector of the invention from a sample, the method comprising:

(a) providing a solid support comprising (i) a matrix and (ii) heparin, wherein the heparin is bound to the matrix;

(b) contacting the solid support with a sample comprising the virus vector so as to bind the virus vector to the solid support; and (c) eluting the bound virus vector from the solid support.

As yet a further aspect, the invention provides the use of a virus vector of the invention in the manufacture of a medicament for the treatment of disease.

These and other aspects of the invention are addressed in more detail in the description of the invention set forth below.

BRIEF DESCRIPTION OF THE DRAWINGS

FIG. 1. List of AAV1 and AAV6 mutants generated by swapping amino acid residues using site-directed mutagenesis.

DETAILED DESCRIPTION OF THE INVENTION

Figure 2:
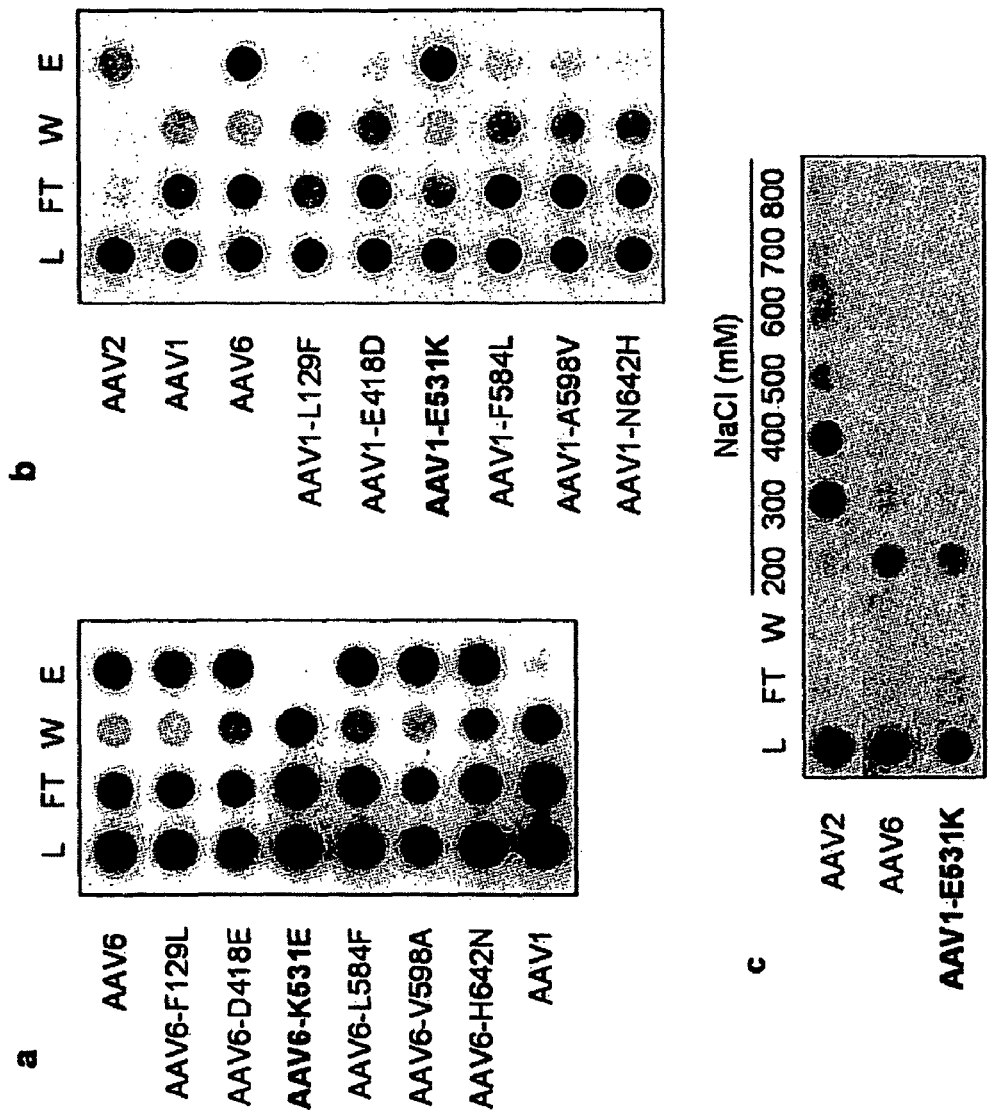
FIGS. 2A-C. (a) Heparin binding profile of AAV6 mutants. (b) Heparin binding profile of AAV1 mutants. (c) Elution profiles of AAV2, AAV6, and AAV1-E531K at different salt concentrations. Mutants at the 531 position are shown in bold letters.

The present inventors have found that parvovirus (including AAV) capsids can be engineered to incorporate small, selective regions from other parvoviruses that confer desirable properties. In the present case, a substitution of a single amino acid that is unique to the AAV6 capsid among AAV capsids that have been characterized to date can confer one or more desirable properties, including desirable properties of AAV6 and/or of other AAVs to another AAV.

The present invention will now be described with reference to the accompanying drawings, in which representative embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

The designation of all amino acid positions in the AAV capsid subunits in the description of the invention and the appended claims is with respect to VP1 capsid subunit numbering.

Except as otherwise indicated, standard methods known to those skilled in the art may be used for the construction of rAAV constructs, modified capsid proteins, packaging vectors expressing the AAV rep and/or cap sequences, and transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

Definitions.

The following terms are used in the description herein and the appended claims:

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The term "parvovirus" as used herein encompasses the family Parvoviridae, including autonomously replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B19 virus, and any other autonomous parvovirus now known or later discovered. Other autonomous parvoviruses are known to those skilled in the art. See, e.g., BERNARD N. FIELDS et al., VIROLOGY, volume 2, chapter 69 (4th ed., Lippincott-Raven Publishers).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, ovine AAV, and any other AAV now known or later discovered. See, e.g., BERNARD N. FIELDS et al., VIROLOGY, volume 2, chapter 69 (4th ed., Lippincott-Raven Publishers). Recently, a number of putative new AAV serotypes and clades have been identified (see, e.g., Gao et al., (2004) *J. Virology* 78:6381-6388; Moris et al., (2004) *Virology* 33-:375-383; and Table 1).

The genomic sequences of the various serotypes of AAV and the autonomous parvoviruses, as well as the sequences of the terminal repeats (TRs), Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC_001358, NC_001540, AF513851, AF513852, AY530579; the disclosures of which are incorporated by reference herein for teaching parvovirus and AAV nucleic acid and amino acid sequences. See also, e.g., Srivistava et al., (1983) *J. Virology* 45:555; Chiorini et al., (1998) *J. Virology* 71:6823; Chiorini et al., (1999) *J. Virology* 73:1309; Bantel-Schaal et al., (1999) *J. Virology* 73:939; Xiao et al., (1999) *J. Virology* 73:3994; Muramatsu et al., (1996) *Virology* 221:208; Shade et al., (1986) *J. Virol.* 58:921; Gao et al., (2002) *Proc. Nat. Acad. Sci. USA* 99:11854; Moris et al., (2004) *Virology* 33-:375-383; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1.

TABLE 1

| Complete Genomes | GenBank Accession Number |
| --- | --- |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_0004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |

TABLE 1-continued

| Complete Genomes | GenBank Accession Number |
|---|---|
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

The term "tropism" as used herein refers to preferential entry of the virus into certain cells or tissues, optionally followed by expression (e.g., transcription and, optionally, translation) of a sequence(s) carried by the viral genome in the cell, e.g., for a recombinant virus, expression of the heterologous nucleotide sequence(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus, from a non-integrated episome, as well as any other form in which the virus may take within the cell.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), but in representative embodiments are either single or double stranded DNA sequences.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide.

As used herein, by "isolate" or "purify" (or grammatical equivalents) a virus vector, it is meant that the virus vector is at least partially separated from at least some of the other components in the starting material.

A "therapeutic polypeptide" is a polypeptide that can alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

By the terms "treat," "treating" or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition and/or prevention or delay of the onset of a disease or disorder. Thus, the terms "treat," "treating" or "treatment of" (or grammatically equivalent terms) refer to both prophylactic and therapeutic regimens.

A "heterologous nucleotide sequence" or "heterologous nucleic acid" is a sequence that is not naturally occurring in the virus. Generally, the heterologous nucleic acid comprises an open reading frame that encodes a polypeptide or non-translated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within an AAV capsid. Alternatively, in some contexts, the term "vector" may be used to refer to the vector genome/vDNA alone.

A "rAAV vector genome" or "rAAV genome" is an AAV genome (i.e., vDNA) that comprises one or more heterologous nucleotide sequences. rAAV vectors generally require only the 145 base terminal repeat(s) (TR(s)) in cis to generate virus. All other viral sequences are dispensable and may be supplied in trans (Muzyczka, (1992) Curr. Topics Microbiol. Immunol. 158:97). Typically, the rAAV vector genome will only retain the minimal TR sequence(s) so as to maximize the size of the transgene that can be efficiently packaged by the vector. The structural and non-structural protein coding sequences may be provided in trans (e.g., from a vector, such as a plasmid, or by stably integrating the sequences into a packaging cell). The rAAV vector genome comprises at least one TR sequence (e.g., AAV TR sequence), optionally two TRs (e.g., two AAV TRs), which typically will be at the 5' and 3' ends of the heterologous nucleotide sequence(s), but need not be contiguous thereto. The TRs can be the same or different from each other.

An "AAV terminal repeat" or "AAV TR" may be from any AAV, including but not limited to serotypes 1, 2, 3, 4, 5, 6, 7, 8, 9, 10 or 11 or any other AAV now known or later discovered. The AAV terminal repeats need not have a wild-type terminal repeat sequence (e.g., a wild-type sequence may be altered by insertion, deletion, truncation or missense mutations), as long as the terminal repeat mediates the desired functions, e.g., replication, virus packaging, integration, and/or provirus rescue, and the like.

The term "terminal repeat" or "TR" includes any viral terminal repeat and synthetic sequences that form hairpin structures and function as an inverted terminal repeat, such as the "double-D sequence" as described in U.S. Pat. No. 5,478, 745 to Samulski et al. The capsid structures of autonomous parvoviruses and AAV are described in more detail in BERNARD N. FIELDS et al., VIROLOGY, volume 2, chapters 69 & 70 (4th ed., Lippincott-Raven Publishers). See also, description of the crystal structure of AAV2 (Xie et al., (2002) Proc. Nat. Acad. Sci. 99:10405-10), AAV4 (Padron et al., (2005) J. Virol. 79: 5047-58), AAV5 (Walters et al., (2004) J. Virol. 78: 3361-71) and CPV (Xie et al., (1996) J. Mol. Biol. 6:497-520 and Tsao et al., (1991) Science 251: 1456-64).

The virus vectors of the invention can further be "targeted" virus vectors (e.g., having a directed tropism) and/or a "hybrid" parvovirus (i.e., in which the rAAV genome and viral capsid are from different parvoviruses) as described in international patent publication WO 00/28004 and Chao et al., (2000) Molecular Therapy 2:619 (the disclosures of which are incorporated herein by reference in their entireties).

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of this invention.

Further, the viral capsid or genome can contain other modifications, including insertions, deletions and/or substitutions.

Accordingly, as used herein, the term "virus vector" encompasses hybrid, targeted and duplexed virus particles, as well as other modified forms of parvoviruses and AAV.

Chimeric Virus Vectors.

The inventors have identified an amino acid within the AAV6 capsid that can be transferred into other AAV capsids to confer a variety of desirable properties including, but not limited to, heparin/heparan sulfate binding, enhanced in vitro transduction, modulation of tropism and/or enhanced in vivo liver transduction. Substitution of this amino acid into other AAV capsids may also confer other desirable properties of AAV6 including improved transduction of skeletal muscle by systemically delivered vector (e.g., by intravenous administration). Transfer of this amino acid into other AAV capsids also facilitates purification by heparin affinity purification (U.S. Pat. No. 6,410,300; Summerford et al., (1998) J. Virol. 72:1438-45). Further, the resulting chimeric virus may have a different immunological profile than the parent virus (e.g., is not recognized by or is only weakly recognized by neutralizing antiserum to the parent virus), thereby allowing for repeat administration to subjects that have developed antibodies against the parent virus.

In representative embodiments, the invention provides a virus vector comprising: (a) an AAV capsid comprising an amino acid substitution that results in a positively charged amino acid at amino acid position 531 in one or more of the AAV1 capsid subunits (VP1 numbering) or at the corresponding amino acid position in other AAV capsid subunits (see, e.g., Table 2); and (b) a recombinant nucleic acid comprising a TR sequence (e.g., AAV TR) and a heterologous nucleic acid sequence; wherein the nucleic acid is packaged within the AAV capsid. Heterologous nucleic acids are as discussed in greater detail herein.

The designation of all amino acid positions in the description of the invention and the appended claims is with respect to VP1 numbering. It will be understood by those skilled in the art that the modifications described herein if inserted into the AAV cap gene will result in modifications in the VP1, VP2 and VP3 capsid subunits. Alternatively, the capsid subunits can be expressed independently to achieve modification in only one or two of the capsid subunits (VP1, VP2, VP3, VP1+VP2, VP1+VP3, or VP2+VP3).

For example, in particular embodiments, the virus vector comprises: (a) an AAV capsid comprising an amino acid substitution that results in a positively charged amino acid at amino acid position 531 in an AAV1 VP3 capsid subunit (VP1 numbering) or at the corresponding amino acid position in other AAV capsid subunits; and (b) a recombinant nucleic acid comprising a TR sequence (e.g., AAV TR sequence) and a heterologous nucleic acid sequence; wherein the nucleic acid is packaged within the AAV capsid.

In exemplary embodiments, the substitution is a glutamic acid to lysine substitution at amino acid position 531 of the AAV1 capsid. Illustrative "corresponding" amino acid positions and substitutions are shown in Table 2 for other AAV serotypes. The nucleic acid and amino acid capsid sequences from a number of AAV are known in the art as described herein (see, e.g., Tables 1 and 2).

TABLE 2

| Mutant[1] | Amino Acid Mutation (VP1 Numbering) | Mutation Position On Virus Genome | NCBI Genome Accession No. |
|---|---|---|---|
| AAV1 E-K | E531K | 3813 G→A | NC 002077 |
| AAV2 E-K | E530K | 3785 G→A | NC 001401 |
| AAV3a E-K | E531K | | |
| AAV3b E-K | E531K | 3798 G→A | NC 001863 |
| AAV4 D-K | D530K | 3847 G→A, 3849 C→A | NC 001829 |
| AAV5 G-K | G517K | 3755 G→A, 3756 G→A, 3757 G→A | NC 006152 |
| AAV7 E-K | E533K | | |
| AAV8 E-K | E533K | 3717 G→A | NC 006261 |
| AAV9 E-K | E531K | | |
| AAV10 E-K | E533K | | |
| AAV11 D-K | D529K | | |

[1]Mutations based on sequence of AAV6 having amino acid 531K (genome position 3798–3800) (NCBI Accession No. AF 028704)

Corresponding amino acid positions in other AAV serotypes or modified AAV capsids will be readily apparent to those skilled in the art using sequence alignment techniques and/or crystal structure analysis (Padron et al., (2005) *J. Virol.* 79:5047-58).

According to the present invention, the substitution is a "selective" amino acid change introduced into the virus capsid. This approach is in contrast to previous work with whole subunit or large domain swaps between AAV serotypes (see, e.g., international patent publication WO 00/28004 and Hauck et al., (2003) *J. Virology* 77:2768-2774). In particular embodiments, a "selective" amino acid change results in the insertion and/or substitution and/or deletion of less than about 20, 18, 15, 12, 10, 9, 8, 7, 6, 5, 4 or 3 contiguous amino acids. In particular embodiments, only two contiguous amino acids or even point mutations (i.e., one amino acid) are inserted and/or substituted into and/or deleted from the capsid subunits.

The virus vectors of the invention comprise a selective amino acid substitution that results in a positively charged amino acid or a cysteine at position 531 of the AAV1 capsid subunits or the corresponding position in other AAV capsids. The virus capsid can further have one or more additional selective amino acid changes (insertions, deletions and/or substitutions) at different positions within the capsid subunits. For example, in particular embodiments, two, three, four or more selective amino acid changes can be introduced into the AAV capsid.

It will be understood by those skilled in the art that the inventive virus vector and virus capsids of the invention exclude those virus vectors or capsids that have the indicated amino acids at the specified positions in their native state (i.e., are not mutants).

The invention contemplates that the chimeric viruses of the invention can be produced by modifying the capsids of any AAV now known or later discovered. Further, the starting AAV that is to be modified can be one of the characterized AAV serotypes or clades, e.g., AAV2, AAV3a or 3b, AAV4, AAV5, AAV8, AAV9, AAV10 or AAV11 (see, e.g., Tables 1 and 2).

Alternatively, the starting virus may already have modifications/alterations as compared with the naturally occurring viruses. Such viruses are also within the scope of the present invention. For example, the starting or parent virus can be a modified AAV as described in U.S. Provisional Application Ser. No. 60/636,126. As another illustrative example, the AAV can be derived from any of the known serotypes or clades, but have a peptide targeting sequence incorporated therein. As yet another possibility, the AAV capsid can comprise capsid subunits from different serotypes. Thus, in particular embodiments, the parent virus comprises a capsid from an AAV serotype or lade that has been modified to comprise sequences that are not from that serotype or clade (e.g., are exogenous) and the virus vector or capsid comprises a positively charged amino acid or a cysteine that has been substituted into the capsid at an amino acid position corresponding to amino acid position 531 of the AAV1 capsid. The "corresponding" amino acid position will be readily apparent to those skilled in the art, for example by using sequence alignment and crystal structure analysis techniques as are well known in the art.

In representative embodiments the positively charged amino acid is a lysine. Alternatively, the positively charged amino acid is an arginine or a histidine. As another option, the positively charged amino acid is a modified or non-naturally occurring amino acid that has a positive charge (e.g., ornithine). It is further contemplated that the substituted amino acid can be a noncanonical amino acid as is known in the art. (See, e.g., Anderson & Schultz "Adaptation of an orthogonal archael leucyl-tRNA and synthetase pair for four-base, amber, and opal suppression" *Biochemistry* 42:9598-9608 (2003); the entire contents of which are incorporated herein for teachings regarding noncanonical amino acids.)

It is further contemplated that additional embodiments of this invention can include a substitution of a cysteine at residue 531 on the AAV1 capsid or at the corresponding amino acid residue in other AAV capsids as described herein. This substitution is based on the rationale that amino acid 531 is present on the surface of the capsid subunit and other amino acid substitutions can be introduced at this site in AAV1 and/or in the corresponding amino acid in other AAV serotypes as described herein to impart various capabilities to the AAV capsid and/or to a virus vector comprising an AAV capsid of this invention.

In some embodiments of this invention, substitution with a cysteine residue at site 531 or the corresponding site would provide a free thiol available for coupling through maleimide or disulfide linker chemistry to a range of fluorophores, gold nanoparticles and radiolabels for imaging applications. Furthermore, substitution of a cysteine residue at site 531 or the corresponding site can allow for site-specific conjugation of polyethylene glycol (PEG) molecules to enable, for example, immune evasion, and can also allow for site-specific conjugation of bifunctional PEG molecules to enable crosslinking of the capsid to protein ligands that will allow retargeting in vivo. Other embodiments include substitution of a cysteine residue at site 531 or the corresponding site for site-specific conjugation of small molecule drugs through cleavable crosslinkers to enable intracellular delivery to specific sites, which in turn can enhance transduction efficiency. For example, the conjugation of proteosomal inhibitors such as doxorubicin or MG132 through cleavable disulfide linkers will allow their site-specific release in the cytosol potentially within proximity of proteasomal machinery.

Thus, in representative embodiments of the invention, the virus vector comprises an AAV capsid comprising an amino acid substitution that results in a positively charged amino acid (e.g., lysine, arginine, histidine) or a cysteine at:

(a) amino acid position 531 of an AAV1 capsid subunit, optionally a lysine or cysteine is substituted at amino acid position 531 of an AAV1 capsid subunit;

(b) amino acid position 530 of an AAV2 capsid subunit, optionally a lysine or cysteine is substituted at amino acid position 530 of an AAV2 capsid subunit;

(c) amino acid position 531 of an AAV3a capsid subunit, optionally a lysine or cysteine is substituted at amino acid position 531 of an AAV3a capsid subunit;

(d) amino acid position 531 of an AAV3b capsid subunits, optionally a lysine or cysteine is substituted at amino acid position 531 of an AAV3b capsid subunit;

(e) amino acid position 530 of an AAV4 capsid subunit, optionally a lysine or cysteine is substituted at amino acid position 530 of an AAV4 capsid subunit;

(f) amino acid position 517 of an AAV5 capsid subunit, optionally a lysine or cysteine is substituted at amino acid position 517 of an AAV5 capsid subunit;

(g) amino acid position 533 of an AAV7 capsid subunit, optionally a lysine or cysteine is substituted at amino acid position 533 of an AAV7 capsid subunits;

(h) amino acid position 533 of an AAV8 capsid subunit, optionally a lysine or cysteine is substituted at amino acid position 533 of an AAV1 capsid subunits;

(i) amino acid position 531 of an AAV9 capsid subunit, optionally a lysine or cysteine is substituted at amino acid position 531 of an AAV9 capsid subunits;

(j) amino acid position 533 of an AAV10 capsid subunit, optionally a lysine or cysteine is substituted at amino acid position 533 of an AAV10 capsid subunit; or (k) amino acid position 529 of an AAV11 capsid subunit, optionally a lysine or cysteine is substituted at amino acid position 529 of an AAV11 capsid subunit.

As discussed above, the AAV capsid subunits can be expressed independently, and the substitution can be made in only one or two of the three AAV capsid subunits, for example, in VP3.

In representative embodiments, the virus vectors of the invention have enhanced binding to heparin and/or heparan sulfate as compared with a parent virus vector that does not have the amino acid substitution. In other embodiments, the virus vector has enhanced transduction of liver as compared with a parent virus vector that does not have the amino acid substitution. Further, the virus vector of the invention can have enhanced transduction of skeletal muscle, optionally when the virus vector is delivered systemically (e.g., intravenously).

Methods of Producing Chimeric Virus Vectors.

The present invention further provides methods of producing the inventive virus vectors. In one particular embodiment, the present invention provides a method of producing a virus vector, comprising providing to a cell, (a) a nucleic acid template comprising (i) at least one heterologous nucleic acid sequence, and (ii) at least one TR sequence (e.g., AAV TR sequence), and (b) AAV sequences sufficient for replication of the nucleic acid template and encapsidation into AAV capsids (e.g., AAV rep sequences and chimeric AAV cap sequences encoding the inventive AAV capsids of the invention). In particular embodiments, the nucleic acid template comprises two AAV ITR sequences, which are located 5' and 3' to the heterologous nucleic acid sequence(s), although they need not be directly contiguous thereto.

The nucleic acid template and AAV rep and cap sequences are provided under conditions such that recombinant virus vector comprising the nucleic acid template packaged within the chimeric AAV capsid is produced in the cell. The method can further comprise the step of collecting the virus vectors from the cell. The virus vector can be collected from the medium and/or by lysing the cells.

The cell can be a cell that is permissive for AAV viral replication. Any suitable cell known in the art may be employed. Mammalian cells are preferred. Also preferred are trans-complementing packaging cell lines that provide functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158:67).

As a further alternative, the rep/cap sequences may be stably incorporated within a cell.

Typically, and preferably, the AAV rep/cap sequences will not be flanked by the TRs, to prevent rescue and/or packaging of these sequences.

In some embodiments of this invention, the TRs can be modified (e.g., truncated, mutated by substitution, deletion, addition, etc.) to impart different characteristics to a recombinant nucleic acid and/or to a virus vector of this invention. For example, non AAV terminal repeat sequences such as those of other parvoviruses (e.g., canine parvovirus (CPV), mouse parvovirus (MVM), human parvovirus B-19) that provide similar function for vector propagation, packaging, and transduction could be used in the vectors of this invention. In some embodiments of this invention, the TR can be modified with portions of non AAV terminal repeat sequences. In other embodiments of this invention, the TR can be substituted with non parvovirus terminal repeats such as an SV40 hair pin sequence that serves as the origin of SV40 replication. These represent only limited examples of modified TRs and other such modifications would be known to one of ordinary skill in the art.

The nucleic acid template can be provided to the cell using any method known in the art. For example, the template may be supplied by a non-viral (e.g., plasmid) or viral vector. In particular embodiments, the nucleic acid template is supplied by a herpesvirus or adenovirus vector (e.g., inserted into the E1a or E3 regions of a deleted adenovirus). As another illustration, Palombo et al., (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the nucleic acid template is provided by a replicating rAAV virus. In still other embodiments, an AAV provirus is stably integrated into the chromosome of the cell.

To obtain maximal virus titers, helper virus functions (e.g., adenovirus or herpesvirus) essential for a productive AAV infection will be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes required for efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper genes embedded in the chromosome or maintained as a stable extrachromosomal element. It is preferred that these helper virus sequences cannot be packaged into AAV virions, e.g., are not flanked by TRs.

Those skilled in the art will appreciate that it may be advantageous to provide the AAV replication and capsid sequences and the helper virus sequences (e.g., adenovirus sequences) on a single helper construct. This helper construct may be a non-viral or viral construct, but is preferably a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector further contains the nucleic acid template. The AAV rep/cap sequences and/or the rAAV template may be inserted into a deleted region (e.g., the E1a or E3 regions) of the adenovirus.

In a further embodiment, the AAV rep/cap sequences and the adenovirus helper sequences are supplied by a single adenovirus helper vector. The rAAV template is provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The rAAV template is provided as a separate replicating viral vector. For example, the rAAV template may be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, it is preferred that the adenovirus helper sequences and the AAV rep/cap sequences are not flanked by AAV ITRs so that these sequences are not packaged into the AAV virions.

Zhang et al., ((2001) *Gene Ther.* 18:704-12) describe a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al., (1999) *Gene Therapy* 6:986 and WO 00/17377, the disclosures of which are incorporated herein in their entireties).

As a further alternative, the virus vectors of the invention can be produced in insect cells using baculovirus vectors to deliver the rep/cap genes and rAAV template as described, for example, by Urabe et al., (2002) *Human Gene Therapy* 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Preferably, deleted replication-defective helper viruses are used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

Chimeric Capsids.

The present invention further encompasses chimeric virus capsids essentially as described above with respect to the chimeric virus vectors, i.e., in the absence of vector genome.

The chimeric virus capsids can be used as "capsid vehicles," as has been described, for example, in U.S. Pat. No. 5,863,541 (the disclosure of which is incorporated by reference herein in its entirety). Molecules that can be packaged by the chimeric virus capsids of this invention and transferred into a cell include heterologous DNA, RNA, polypeptides, small organic molecules, or combinations of the same.

Heterologous molecules are defined as those that are not naturally found in an AAV infection, e.g., those not encoded by a wild-type AAV genome. Further, therapeutically useful molecules can be associated with the outside of the chimeric virus capsid for transfer of the molecules into host target cells. Such associated molecules can include DNA, RNA, small organic molecules, carbohydrates, lipids and/or polypeptides. In one embodiment of the invention the therapeutically useful molecule is covalently linked (i.e., conjugated or chemically coupled) to the capsid proteins. Methods of covalently linking molecules are known by those skilled in the art.

The chimeric virus capsids of the invention also find use in raising antibodies against the novel capsid structures. As a further alternative, an exogenous amino acid sequence may be inserted into the chimeric virus capsid for antigen presentation to a cell, e.g., for administration to a subject to produce an immune response to the exogenous amino acid sequence.

In other embodiments, the virus capsids can be administered to block certain cellular sites prior to or concurrently with (e.g., within minutes or hours of each other) administration of a virus vector delivering a polypeptide or RNA of interest. For example, the inventive capsids can be delivered to block cellular receptors on liver cells and a delivery vector can be administered subsequently or concurrently, which may reduce transduction of liver cells, and enhance transduction of other targets (e.g., skeletal muscle).

According to some embodiments, chimeric virus capsids can be administered to a subject prior to or concurrently with an AAV vector or virus vector according to the invention. Further, the invention provides compositions and pharmaceutical formulations comprising the inventive chimeric virus capsids and an AAV vector or chimeric virus vector of the invention.

The invention also provides nucleic acids (optionally, isolated nucleic acids) encoding the chimeric virus capsids and capsid subunits of the invention. Further provided are vectors comprising the nucleic acids, and cells (in vivo or in culture) comprising the nucleic acids and/or vectors of the invention. Such nucleic acids, vectors and cells can be used, for example, as reagents (e.g., helper packaging constructs or packaging cells) for the production of chimeric virus capsids or vectors as described herein.

Virus capsids according to the invention can be produced using any method known in the art, e.g., by expression from a baculovirus (Brown et al., (1994) *Virology* 198:477-488).

Purification of Chimeric Virus Vectors and Virus Capsids with Heparin.

The present invention provides a universal method for purifying AAV capsids and virus vectors comprising AAV capsids based on binding to heparin or other glycosaminoglycans such as heparan sulfate, dextran sulfate and dermatan sulfate. Heparin affinity matrices, which are well known in the art, are particularly convenient for commercial and clinical use. Methods are known in the art for purifying AAV based on affinity for heparin and other glycosaminoglycans (U.S. Pat. No. 6,410,300; Summerford et al., (1998) *J. Virol.* 72:1438-45). Purification with heparin or other glycosaminoglycans provides a highly pure preparation, relatively free of contaminating adenovirus, with a low particle-to-infectivity ratio. These methods can also be used to concentrate AAV preparations.

In particular embodiments, the present invention provides a method of purifying a virus vector from a sample, the method comprising: (a) providing a solid support comprising (i) a matrix, and (ii) heparin or other glycosaminoglycan such as heparan sulfate, dermatan sulfate and/or dextran sulfate, wherein the heparin or other glycosaminoglycan is bound to the matrix; (b) contacting the solid support with the sample containing a virus vector or capsid of the invention to bind the virus vector of capsid to the solid support; and (c) eluting the bound virus vector or capsid from the solid support. The purified virus vector or capsid can further be collected.

The sample can be any sample that contains, or is suspected of containing, a virus vector or virus capsid of the invention. The sample can be a crude sample (e.g., a lysed cell preparation), a partially-purified sample (e.g., the sample may be the result of ammonium sulfate precipitation, dialysis, density gradient purification [for example, with sucrose or iodixanol] or any other purification method) or may be a relatively pure preparation (e.g., the method is practiced to reduce sample volume and concentrate the sample).

For example, in particular embodiments, a virus vector is produced in cell culture. The cells can be lysed, for example, by detergent, freeze-thaw cycles and/or sonication. The virus vector can be partially purified away from cell debris by tangential flow filtration. The virus vector can then be further purified over a heparin affinity column (e.g., by fast protein liquid chromatography [FPLC]), optionally followed by a further purification or concentration step(s).

In particular embodiments of the invention, heparin and/or other glycosaminoglycan is immobilized to a matrix to create an affinity purification solid support. The immobilized heparin and/or other glycosaminoglycan can be contacted with the sample containing the virus vector or virus capsid (or suspected of containing the virus vector or virus capsid) by any method known in the art. In representative embodiments, the solid support is packed into a chromatography column, and the virus vector or capsid is purified from the sample by affinity chromatography. Chromatography can be carried out using conventional columns or by HPLC (high performance liquid chromatography) or FPLC. Alternatively, the virus vector can be purified from the sample in a batch method. To illustrate, the sample can be contacted with beads (e.g., magnetic beads) comprising the heparin or other glycosaminoglycan and the beads concentrated (for example, by centrifugation) to purify the virus from the sample. Binding of the virus vector to magnetic beads bearing heparin or another glycosaminoglycan is particularly useful for concentrating dilute preparations.

Any suitable method for immobilization of molecules (e.g., by adsorption, by electrostatic interactions, by covalent bonds) and matrix available to those skilled in the art may be employed in carrying out the present invention (see, e.g., Methods in Molecular Biology, Protein Purification Protocols (Shawn Doonan ed., 1996)). Matrices for use according to the present invention encompass solid and semi-solid matrices. Exemplary matrices include beads formed from glass, silica, alumina, ground corn grits, cellulose, agarose, polyacrylamide, or CELITE™ (a commercially available form of diatomaceous earth).

Typically, the matrix is modified to bear reactive groups to facilitate the immobilization reaction. For example, primary amine groups can be attached to the matrix by using silanes for siliceous or alumina-based supports. The attached primary amine groups are activated by glutaraldehyde or other activating agent prior to the addition of the ligand. Crosslinking of the covalently bound affinity ligand is optional.

Methods for forming heparinized matrices are known in the art and include both non-covalent and covalent coupling techniques. V. D. Nadkarni et al., (1997) *BioTechniques* 23:382; A. A. Farooqui et al., (1983) *Adv. Chromatogr.* 23:127; O. Larm, (1983) *Biomater. Med. Devices Artif. Organs* 11:161; R. J. Linhardt, Chemical and enzymatic methods for the depolymerization and modification of heparin, p. 385-401. In H. Ogura et al. (Eds.), Carbohydrates—Synthetic Methods and Applications in Medicinal Chemistry. Kodansha, Ltd., Tokyo; J. Liu et al., (1994) *J. Pharm. Sci.* 83:1034; V. D. Nadkarni et al., (1994) *Anal. Biochem.* 222:59-67). Heparin may be covalently coupled through aldehyde groups at the reducing end of heparin using reductive amination to amine-functionalized matrices or by reaction to matrices bearing hydrazido groups. Solid supports bearing receptor-like molecules according to the present invention may also be obtained commercially (e.g., Heparin-Agarose Type I, Heparin-Agarose type II-S, Heparin-Agarose Type III-S, all from Sigma Chemical Co., and Affi-Gel Heparin Gel from Bio-Rad Laboratories).

As a further alternative, an affinity support can be formed by immobilizing an antibody (e.g., a monoclonal or polyclonal antibody or fragment thereof such as a Fab fragment) to a matrix, where the antibody binds to the heparin and/or other glycosaminoglycan. The heparin and/or other glycosaminoglycan is immobilized to the matrix through interaction with the antibody prior to contacting the solid support with the sample.

As yet a further alternative, the matrix can be a polymeric surface (e.g., a polystyrene, polypropylene, or polyethylene tube or plate) with the receptor-like molecule immobilized thereto. The matrix can also be a material such as fiberglass, cellulose acetate, nitrocellulose, or nylon. This embodiment most readily finds application in purifying and/or concentrating relatively small quantities of the virus for analytical and/or diagnostic purposes or for determining virus titers.

Recombinant Virus Vectors.

The virus vectors of the present invention are useful for the delivery of nucleic acids to cells in vitro, ex vivo, and in vivo. In particular, the virus vectors can be advantageously employed to deliver or transfer nucleic acids to animal, including mammalian, cells.

Any heterologous nucleic acid sequence(s) may be delivered in the chimeric virus vectors of the present invention. Nucleic acids of interest include nucleic acids encoding polypeptides, including therapeutic (e.g., for medical or veterinary uses) or immunogenic (e.g., for vaccines) polypeptides.

Therapeutic polypeptides include, but are not limited to, cystic fibrosis transmembrane regulator protein (CFTR), dystrophin (including the protein product of dystrophin minigenes, see, e.g, Vincent et al., (1993) *Nature Genetics* 5:130; U.S. Patent Publication No. 2003/017131, utrophin (Tinsley et al., (1996) *Nature* 384:349), clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $\alpha_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), lysosomal acid α-glucosidase, α-galactosidase A, receptors (e.g., the tumor necrosis growth factorα soluble receptor), anti-inflammatory factors such as IRAP, anti-myostatin proteins, aspartoacylase, monoclonal antibodies (including single chain monoclonal antibodies; an exemplary Mab is the Herceptin® Mab). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof.

Heterologous nucleotide sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Alternatively, in particular embodiments of this invention, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. Nos. 6,013,487; 6,083,702), interfering RNAs (RNAi) including siRNA that mediate gene silencing (see, Sharp et al., (2000) *Science* 287:2431) other non-translated RNAs, such as "guide" RNAs (Gorman et al., (1998) *Proc. Nat. Acad. Sci. USA* 95:4929; U.S. Pat. No. 5,869,248 to Yuan et al.), and the like. Exemplary untranslated RNAs include RNAi against a multiple drug resistance (MDR) gene product (e.g., to treat tumors and/or for administration to the heart to prevent damage by chemotherapy), RNAi against myostatin (e.g., for Duchenne muscular dystrophy), and/or RNAi against VEGF (e.g., to treat tumors).

The virus vector may also comprise a heterologous nucleotide sequence that shares homology with and recombines with a locus on a host chromosome. This approach can be utilized, for example, to correct a genetic defect in the host cell.

The virus vector of the present invention can also be used to target specific organs of the body to deliver a heterologous nucleotide sequence of this invention and/or to impart other beneficial (e.g., therapeutic) effects. Such organs can include but are not limited to brain, muscle, heart, lung, liver, eye, kidney, pancreas, intestines, stomach, vessels, bone and the like, as are known in the art. In yet additional embodiments, the virus vector of this invention can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue, from which it can migrate into neurons.

The present invention also provides virus vectors that express an immunogenic peptide and/or polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccines is known in the art (see, e.g., Miyamura et al., (1994) *Proc. Nat. Acad. Sci USA* 91:8507; U.S. Pat. No. 5,916,563 to Young et al., U.S. Pat. No. 5,905,040 to Mazzara et al., U.S. Pat. No. 5,882,652, U.S. Pat. No. 5,863,541 to Samulski et al.; the disclosures of each of which are incorporated herein in their entireties by reference). The antigen may be presented in the parvovirus capsid. Alternatively, the antigen may be expressed from a heterologous nucleic acid introduced into a recombinant vector genome. Any immunogen of interest as described herein and/or as is known in the art can be provided by the virus vector of the present invention.

An immunogenic peptide, polypeptide or immunogen can be any peptide, polypeptide and/or immunogen suitable for eliciting an immune response and/or protecting the subject against an infection and/or disease, including, but not limited to, microbial, bacterial, protozoal, parasitic, fungal and/or viral infections and diseases. For example, the immunogen can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogen can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogen can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogen can be any tumor or cancer cell antigen. Preferably, the tumor or cancer antigen is expressed on the surface of the cancer cell. Exemplary cancer and tumor cell antigens are described in S. A. Rosenberg (*Immunity* 10:281 (1991)). Other illustrative cancer and tumor antigens include, but are not limited to: BRCA1 gene product, BRCA2 gene product, gp100, tyrosinase, GAGE-1/2, BAGE, RAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.,* 180:347; Kawakami et al., (1994) *Cancer Res.* 54:3124) including MART-1 (Coulie et al., (1991) *J. Exp. Med.* 180:35), gp100 (Wick et al., (1988) *J. Cutan. Pathol.* 4:201) and MAGE antigen, MAGE-1, MAGE-2 and MAGE-3 (Van der Bruggen et al., (1991) *Science,* 254:1643); CEA, TRP-1, TRP-2, P-15 and tyrosinase (Brichard et al., (1993) *J. Exp. Med.* 178:489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma, sarcoma, lung cancer, liver cancer, colon cancer, non-Hodgkin's lymphoma, Hodgkin's lymphoma, leukemias, uterine cancer, breast cancer, prostate cancer, ovarian cancer, cervical cancer, bladder cancer, kidney cancer, pancreatic cancer and any other cancer or malignant condition now known or later identified (see, e.g., Rosenberg, (1996) *Ann. Rev. Med.* 47:481-91).

As a further alternative, the heterologous nucleotide sequence may encode any polypeptide that is desirably produced in a cell in vitro, ex vivo, or in vivo. For example, the virus vectors may be introduced into cultured cells and the expressed gene product isolated therefrom.

It will be understood by those skilled in the art that the heterologous nucleotide sequence(s) of interest may be operably associated with appropriate control sequences. For example, the heterologous nucleic acid may be operably associated with expression control elements, such as transcription/translation control signals, origins of replication, polyadenylation signals, internal ribosome entry sites (IRES), promoters, enhancers, and the like.

Those skilled in the art will appreciate that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced.

Promoter/enhancer elements that are native to the target cell or subject to be treated are most preferred. Also preferred are promoters/enhancer elements that are native to the heterologous nucleic acid sequence. The promoter/enhancer element is chosen so that it functions in the target cell(s) of interest. Mammalian promoter/enhancer elements are also preferred. The promoter/enhance element may be constitutive or inducible.

Inducible expression control elements are preferred in those applications in which it is desirable to provide regulation over expression of the heterologous nucleic acid sequence(s). Inducible promoters/enhancer elements for gene delivery are preferably tissue-specific promoter/enhancer elements, and include muscle specific (including cardiac, skeletal and/or smooth muscle), neural tissue specific (including brain-specific), eye (including retina-specific and cornea-specific), liver specific, bone marrow specific, pancreatic specific, spleen specific, and lung specific promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) will be transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering heterologous nucleotide sequences into a broad range of cells, including dividing and non-dividing cells. The virus vectors can be employed to deliver a nucleotide sequence of interest to a cell in vitro, e.g., to produce a polypeptide in vitro or for ex vivo gene therapy. The vectors are additionally useful in a method of delivering a nucleotide sequence to a subject in need thereof, e.g., to express an immunogenic or therapeutic polypeptide. In this manner, the polypeptide can thus be produced in vivo in the subject. The subject can be in need of the polypeptide because the subject has a deficiency of the polypeptide, or because the production of the polypeptide in the subject may impart some therapeutic effect, as a method of treatment or otherwise, and as explained further below.

The virus vectors can also be used to produce a polypeptide of interest in cultured cells or in a subject (i.e., using the subject as a bioreactor to produce the polypeptide).

In general, the parvovirus vectors of the present invention may be employed to deliver any foreign nucleic acid with a biological effect to treat or ameliorate the symptoms associated with any disorder related to gene expression. Alternatively, the invention can be used to treat any disease state for which it is beneficial to deliver a therapeutic polypeptide. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product), diabetes mellitus (insulin), muscular dystrophies including Duchenne (dystrophin, mini-dystrophin, insulin-like growth factor 1, a sarcoglycan [e.g., α, β, γ], RNAi against myostatin) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic defects, congenital emphysema (α1-antitrypsin), Lesch-Nyhan Syndrome (hypoxanthine guanine phosphoribosyl transferase), Niemann-Pick disease (sphingomyelinase), Tays Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1), phospholamban, serca2a, zinc finger proteins that regulate the phospholamban gene, Barkct, β2-adrenergic receptor, β2-adrenergic receptor kinase (BARK), phosphoinositide-3 kinase (PI3 kinase), calsarcin, etc.), arthritis (insulin-like growth factors), joint disorders (insulin-like growth factors), intimal hyperplasia (e.g., by delivering enos, inos), improve survival of heart transplants (superoxide dismutase), AIDS (soluble CD4), muscle wasting (insulin-like growth factor 1), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including RANKL and/or VEGF) can be administered with a bone allograph, for example, following a break or surgical removal in a cancer patient.

Gene transfer has substantial potential use in understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus virus vectors according to the present invention permit the treatment of genetic diseases. As used herein, a disease state is treated by partially or wholly remedying the deficiency or imbalance that causes the disease or makes it more severe. The use of site-specific recombination of nucleic sequences to cause mutations or to correct defects is also possible.

The virus vectors according to the present invention may also be employed to provide an antisense nucleic acid or RNAi (e.g., siRNA) to a cell in vitro or in vivo. Expression of the antisense nucleic acid or RNAi in the cell diminishes expression of a particular target protein by the cell. Accordingly, antisense nucleic acids or RNAi may be administered to decrease expression of a particular protein in a subject in need thereof. Antisense nucleic acids or RNAi may also be administered to cells in vitro to regulate cell physiology, e.g., to optimize cell or tissue culture systems.

Further, the virus vectors according to the instant invention find use in diagnostic and screening methods, whereby a gene of interest is transiently or stably expressed in a cell culture system, or alternatively, a transgenic animal model.

The virus vectors of the present invention can also be used for various nontherapeutic purposes, including but not limited to use in protocols to assess gene targeting, clearance, transcription, translation, etc., as would be known to one of ordinary skill in the art. The vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present invention may be used to produce an immune response in a subject. According to this embodiment, a virus vector comprising a heterologous nucleic acid sequence encoding an immunogen may be administered to a subject, and an active immune response is mounted by the subject against the immunogen. Immunogens are as described hereinabove. In some embodiments, a protective immune response is elicited.

Alternatively, the virus vector may be administered to a cell ex vivo and the altered cell is administered to the subject. The heterologous nucleotide sequence is introduced into the cell, and the cell is administered to the subject, where the heterologous nucleotide sequence encoding the immunogen is preferably expressed and induces an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment of disease, in particular cancer or tumors (e.g., by causing regression of a cancer or tumor and/or by preventing metastasis and/or by preventing growth of metastatic nodules). The protective effects may be complete or partial, as long as the benefits of the treatment outweigh any disadvantages thereof.

According to the foregoing methods of inducing an immune response in a subject, the virus vector comprising the heterologous nucleotide sequence can be administered in an immunogenically effective amount, as described below.

The virus vectors of the present invention may also be administered for cancer immunotherapy by administration of a virus vector expressing cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleotide sequence encoding the cancer cell antigen, for example to treat a patient with cancer. The virus vector may be administered to a subject in vivo or by using ex vivo methods, as described herein. Alternatively, the cancer antigen can be expressed in the virus capsid or be otherwise associated with the virus capsid as described above.

As another alternative, any other therapeutic nucleic acid (e.g., RNAi) or polypeptide (e.g., cytokine) known in the art can be administered to treat cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to, leukemias, lymphomas, colon cancer, renal cancer, liver cancer, breast cancer, lung cancer, prostate cancer, ovarian cancer, melanoma, and the like. Preferred are methods of treating and preventing tumor-forming cancers.

The term "tumor" is also understood in the art, for example, as an abnormal mass of undifferentiated cells within a multicellular organism. Tumors can be malignant or benign. Preferably, the methods disclosed herein are used to prevent and treat malignant tumors.

By the terms "treating cancer" or "treatment of cancer," it is intended that the severity of the cancer is reduced or the cancer is prevented or at least partially eliminated. Preferably, these terms indicate that metastasis of the cancer is prevented or reduced or at least partially eliminated. It is further preferred that these terms indicate that growth of metastatic nodules (e.g., after surgical removal of a primary tumor) is prevented or reduced or at least partially eliminated. By the terms "prevention of cancer" or "preventing cancer" it is intended that the methods at least partially eliminate or reduce the incidence or onset of cancer. Alternatively stated, the onset of cancer in the subject may be slowed, controlled, decreased in likelihood or probability, or delayed.

In particular embodiments, cells may be removed from a subject with cancer and contacted with virus vectors according to the instant invention. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleotide sequence encoding a cytokine may be delivered to the subject using a suitable vector, and the cytokine produced in vivo.

Subjects, Pharmaceutical Formulations, and Modes of Administration.

Virus vectors according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles, and adults.

In particular embodiments, the present invention provides a pharmaceutical composition comprising a virus vector of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleotide sequence to a cell in vitro. The virus particles may be introduced into the cells at the appropriate multiplicity of infection according to standard transduction methods appropriate for the particular target cells. Titers of virus to administer can vary, depending upon the target cell type and number, and the particular virus vector, and can be determined by those of skill in the art without undue experimentation. Preferably, at least about $10^3$ infectious units, more preferably at least about $10^5$ infectious units are introduced to the cell.

The cell(s) into which the virus vector is introduced may be of any type, including but not limited to neural cells (including cells of the peripheral and central nervous systems, in particular, brain cells such as neurons and oligodendricytes), lung cells, cells of the eye (including retinal cells, retinal pigment epithelium, and corneal cells), epithelial cells (e.g., gut and respiratory epithelial cells), muscle cells, dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. Alternatively, the cell may be any progenitor cell. As a further alternative, the cell can be a stem cell (e.g., neural stem cell, liver stem cell). As still a further alternative, the cell may be a cancer or tumor cell. Moreover, the cells can be from any species of origin, as indicated above.

Dendritic cells (DC), which are refractory to wtAAV vectors (Jooss et al., J. Virol. (1998) 72:4212), are permissive for the viral vectors of the present invention. Accordingly, as yet a further aspect of this invention, provided herein are methods of introducing a virus vector of this invention to a DC, thereby delivering a heterologous nucleotide sequence to a DC, e.g., to induce an immune response to a peptide, polypeptide and/or immunogen encoded by the heterologous nucleotide sequence. In some embodiments, the heterologous nucleotide sequence encodes an antigen from an infectious agent and/or a cancer antigen. Thus, the virus vector of this invention can be used in some embodiments as a vaccine and/or in vaccine development and preparation.

The virus vector may be introduced into cells in vitro for the purpose of administering the modified cell to a subject. In particular embodiments, the cells have been removed from a subject, the virus vector is introduced therein, and the cells are then replaced back into the subject. Methods of removing cells from subject for treatment ex vivo, followed by introduction back into the subject are known in the art (see, e.g., U.S. Pat. No. 5,399,346; the disclosure of which is incorporated herein in its entirety). Alternatively, the recombinant virus vector is introduced into cells from another subject, into cultured cells, or into cells from any other suitable source, and the cells are administered to a subject in need thereof.

Suitable cells for ex vivo gene therapy are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a therapeutically effective amount in combination with a pharmaceutical carrier.

A "therapeutically effective" amount as used herein is an amount that is sufficient to provide some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

In some embodiments, cells that have been transduced with a virus vector may be administered to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vector to subjects. Administration of the virus vectors according to the present invention to a human subject or an animal in need thereof can be by any means known in the art. Preferably, the virus vector is delivered in a therapeutically effective dose in a pharmaceutically acceptable carrier.

The virus vectors of the invention can further be administered to elicit an immunogenic response (e.g., as a vaccine). Typically, vaccines of the present invention comprise an immunogenically effective amount of virus in combination with a pharmaceutically acceptable carrier. Preferably, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vector to be administered to a subject depends upon the mode of administration, the disease or condition to be treated, the individual subject's condition, the particular virus vector, and the nucleic acid to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$ transducing units or more, preferably about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, vaginal, transmucosal, topical, intranasal, intrathecal, intraocular, transdermal, in utero (or in ovo), inhalation, parenteral (e.g., intravenous, subcutaneous, intradermal, intramuscular, and intraarticular) administration, and the like, as well as direct tissue or organ injection.

Injectables can be prepared in conventional forms, either as liquid solutions or suspensions, solid forms suitable for solution or suspension in liquid prior to injection, or as emulsions. Alternatively, one may administer the virus vector in a local rather than systemic manner, for example, in a depot or sustained-release formulation. Further, the virus vector can be delivered adhered to a surgically implantable matrix (e.g., as described in U.S. Patent Publication No. US-2004-0013645-A1).

The virus vectors disclosed herein may be administered to the lungs of a subject by any suitable means, but are preferably administered by administering an aerosol suspension of respirable particles comprised of the virus vectors, which the subject inhales. The respirable particles may be liquid or solid. Aerosols of liquid particles comprising the virus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors may likewise be produced with any solid particulate medicament aerosol generator, by techniques known in the pharmaceutical art.

Having described the present invention, the same will be explained in greater detail in the following examples, which are included herein for illustration purposes only, and which are not intended to be limiting to the invention.

EXAMPLE 1

There are six amino acid residues that differ between the AAV1 and AAV6 VP1 capsid subunits. To identify potential residues that contribute to heparan sulfate (HS) binding by AAV6, we generated a series of AAV1 and AAV6 mutants by performing QuikChange® site-directed mutagenesis (Stratagene) on plasmids pXR1 (Rabinowitz et al., (2002) *J. Virol.* 76:791-801) and pXR6 (gift from Dr. Joseph Rabinowitz) as per manufacturer instructions. All mutants were sequenced prior to use. Positions of the six amino acids (5 located in Vp3 and 1 in Vp1) that were swapped between AAV1 and AAV6 capsids are described in FIG. 1. Mutant viruses packaging the GFP transgene were produced in 293 cells using the triple-plasmid transfection protocol and purified on CsCl gradients (Xiao et al., (1998) *J. Virol.* 72:2224-32). Peak fractions and viral titers were determined by dot blot hybridization using a radiolabeled GFP transgene probe (data not shown). Binding of parental AAV1, 2, 6, and AAV1/AAV6 mutants to heparin-conjugated agarose type I (H-6508; Sigma) was analyzed by loading affinity columns (Bio-Rad microspin column) with $5 \times 10^{10}$ particles of each viral stock in 500 µL Ringer's saline solution (RSS) followed by the sequential collection of fractions from flow-through, wash with RSS, and elution with RSS containing 800 mM NaCl. The number of mutant or parental AAV particles present in each fraction was determined by dot blot hybridization.

As shown in FIG. 2 (panel a), the heparin column elution profile of the AAV6-K531E mutant is identical to that of AAV1, suggesting an attenuation of heparin binding ability. The remaining five amino acid changes, however, fail to alter the ability of AAV6 to bind heparin. These results are further corroborated in FIG. 2 (panel b), where the reciprocal change in AAV1-E531K imparts heparin-binding characteristics onto the AAV1 capsid similar to wild-type (wt) AAV2 and AAV6. Swapping other amino acid residues from wt AAV6 onto AAV1 does not affect heparin binding. Further, elution of AAV capsids from heparin agarose columns using different salt concentrations suggests that AAV6 and AAV1-E531K bind heparin with slightly lower affinity (200-300 mM) compared to parental AAV2 (300-400 mM). Taken together, these data suggest that Lysine 531 is the core residue at a low-affinity HS binding site on the AAV6 capsid.

Figure 3:
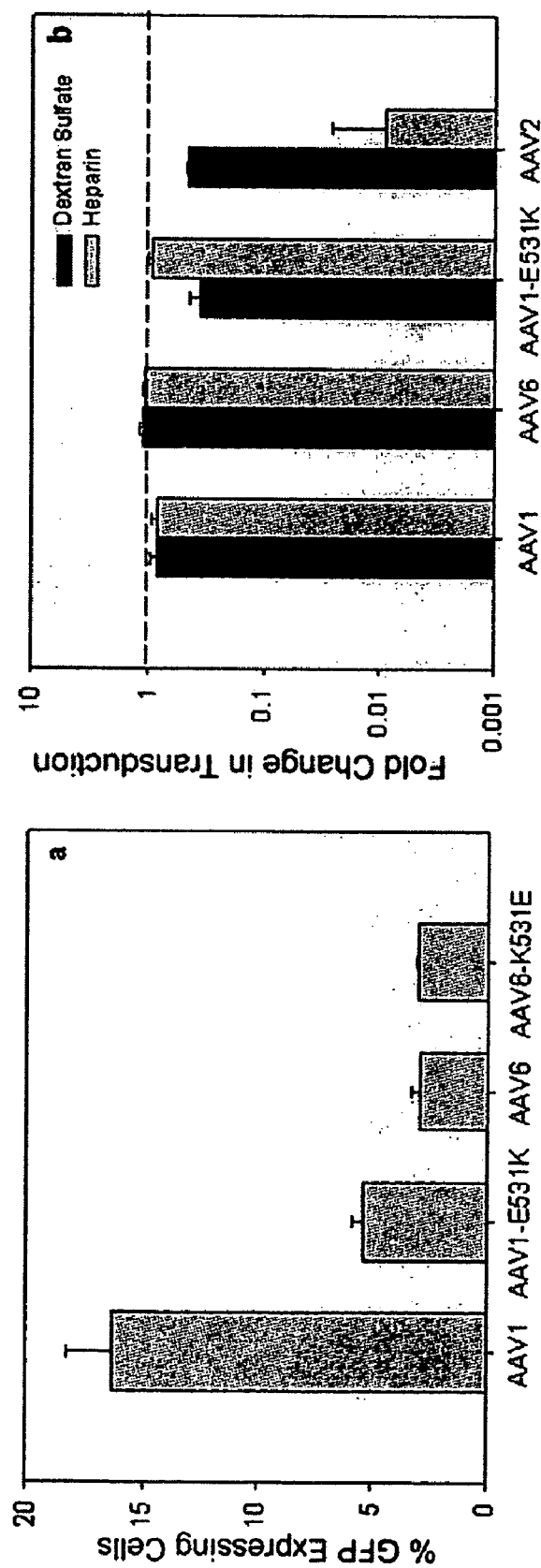
FIGS. 3A-B. (a) Transduction profiles (GFP expression) of parental AAV-1 and AAV6 compared with mutants AAV1-E531K and AAV6-K531E. (b) Fold-decrease in transduction efficiencies of AAV1, AAV6, AAV1-E531K, and AAV2 upon co-incubation with soluble heparin or dextran sulfate. The dotted line represents the normalized transduction efficiencies of the corresponding AAV vectors in the absence of heparin and dextran sulfate.

Since the E531K modification in type 1 conferred HS binding, we next addressed the influence of mutations at the 531 position and that of soluble anionic glycosaminoglycans on the transduction efficiency of wt and mutant AAV1 and 6 viruses. Briefly, viral particles were pre-incubated with soluble heparin, dextran sulfate, or PBS for 1 h at 37° C. After pre-incubation, HeLa cells were infected with wt or mutant AAV capsids in the presence or absence of heparin (30 µg/ml) and dextran sulfate (30 µg/ml) at 1000 vector genomes/cell and co-infected with adenovirus dl309 at an MOI of 15. At 24 h post-transduction, cells were harvested and scored for GFP expression using flow cytometry. Our group and others have shown that AAV1 transduces some mammalian cells in vitro better than AAV6 (Grimm et al., (2003). *Mol Ther* 7:839-50; Grimm et al., (2003) *Blood* 102:2412-9). As shown in FIG. 3 (panel a), the transduction efficiency of AAV1-E531K, in the absence of exogenous factors, is reduced by ~3-fold when compared to wt AAV1. This reduction is equal to wt AAV6, suggesting the ability to bind HS may influence in vitro transduction. In contrast, the transduction level for the AAV6-K531E mutant remains unaltered. These observations suggest that amino acid residue(s) other than AAV1 E531 are responsible for the enhanced in vitro transduction seen with wt AAV1. The effect of soluble heparin and dextran sulfate on AAV1, AAV6, and AAV1 E53 K was assessed in a similar fashion. As shown in FIG. 3 (panel b), transduction by AAV1 and 6 is unaffected upon co-incubation of viral particles with heparin or dextran sulfate. However, transduction efficiency of the AAV1-E531K mutant, although unaffected by heparin, was reduced by half in the presence of dextran sulfate possibly due to non-specific electrostatic interactions. Although E531K will confer HS binding to type 1, it is apparent that the remaining five amino acids (corresponding to AAV6) must prevent non-specific electrostatic interaction seen by addition of dextran sulfate (AAV1 E531K). Lastly, transduction by AAV2, which served as positive control, was reduced approximately 100-fold in the presence of heparin and to a lesser extent (~2-fold) by dextran sulfate, consistent with previously published studies (Summerford et al., (1998) *J. Virol.* 72:1438-45).

In summary, of the six amino acids that differ between AAV type 1 and 6, we have identified a single amino acid (K531) as essential for conferring the HS-binding characteristics of AAV6. Introduction of an E531K change in AAV1 imparts a heparin-binding ability similar to AAV6 and, in turn alters transduction efficiency in vitro. These observations suggest that a minimum basic footprint is required to facilitate heparin binding through electrostatic interactions, although a structural configuration is likely important for efficient utilization as a cell surface receptor. Based on a collective interpretation of results and conservation of amino acids in this region, it was envisioned that a E531K change in other serotypes would confer heparin binding phenotypes.

EXAMPLE 2

Figure 4:
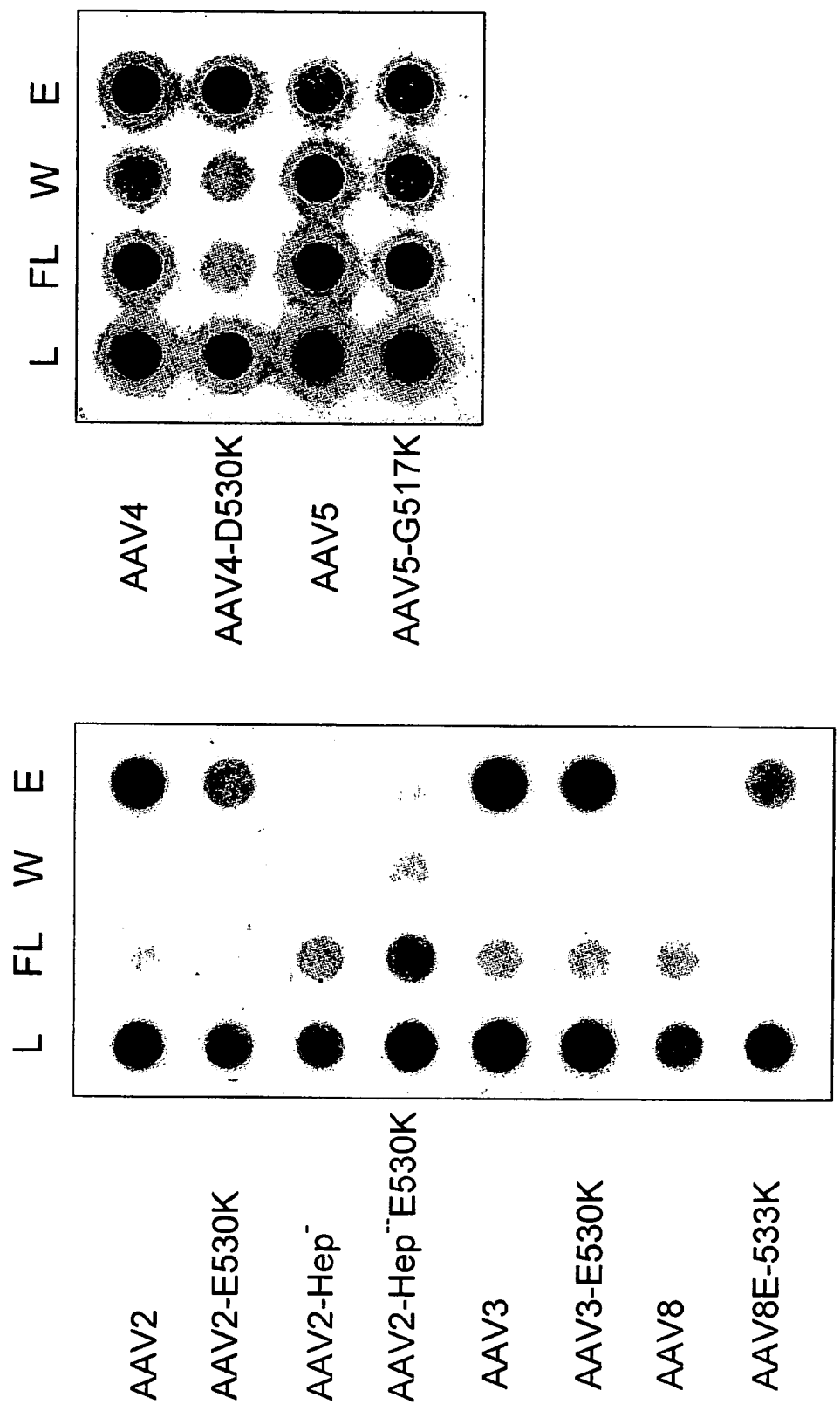
FIG. 4. A D530K AAV4 VP1 subunit mutant and a E533K AAV8 VP1 subunit mutant demonstrate heparin binding. The amino acid positions correspond to position 531 in AAV6.
Figure 5:
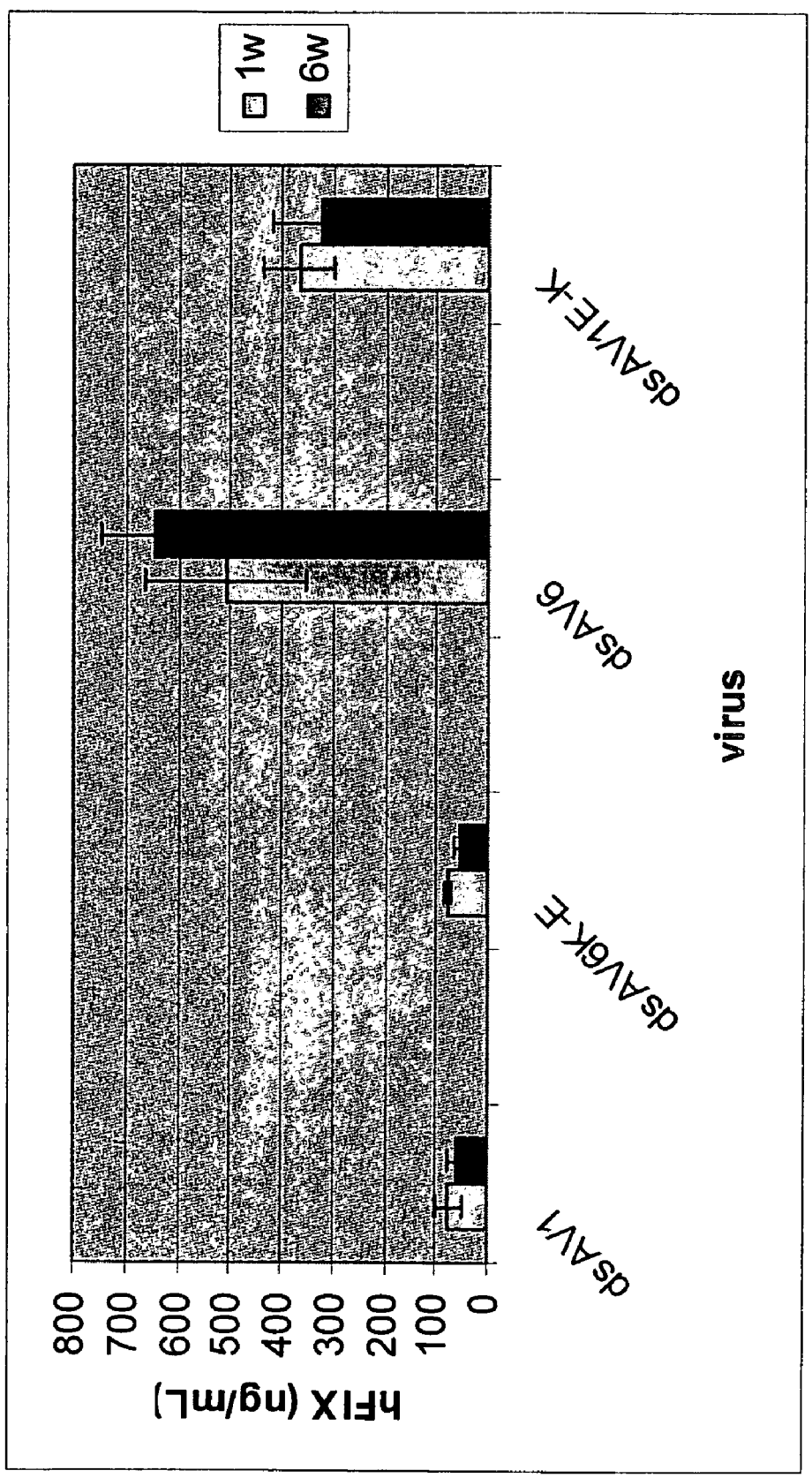
FIG. 5. Plasma human factor IX (hFIX) levels at 1 and 6 weeks following administration to 6-week-old male mice of $5 \times 10^{10}$ particles of a double-stranded vector containing a human factor IX (hFIX) expression cassette driven by a liver-specific promoter packaged in AAV1, AAV1-E531K, AAV6, or AAV6-K531E capsid shells.

AAV1, AAV4 and AAV8 serotypes do not bind HS or heparin. We describe above that a E531K mutation in the AAV1 VP1 capsid subunit conferred heparin binding on AAV1. Further studies have shown that a D530K AAV4 VP1 subunit mutant and a E533K AAV8 VP1 subunit mutant also demonstrate heparin binding (FIG. 4). The amino acid positions correspond to position 531 in AAV6.

Further, AAV2 and AAV3b already exhibit heparin-binding ability. Nonetheless, an enhancement in heparin binding was observed in E530K AAV2 and E531K AAV3b VP1 capsid mutants. Again, these amino acid positions correspond to position 531 in AAV6.

EXAMPLE 3

In vivo transduction data demonstrate that changing the glutamic acid (E) residue at position 531 of AAV1 to the lysine (K) found at that same position in AAV6 increased liver transduction of the E531K AAV1 mutant as compared with the parental AAV1 virus.

A double-stranded genome derived from AAV2 (McCarty et al., (2003) *Gene Ther.* 10: 2112-8) containing a human factor IX (hFIX) expression cassette driven by a liver-specific promoter was packaged into AAV1, AAV1-E531K, AAV6 and AAV6-K531E capsid shells, respectively. All vectors were titered by standard dot blot method. For assessment of in vivo transduction, vectors were infused into the portal vein of 6-week-old male C57Bl/6 mice (Jackson Laboratories, Bar Harbor, Me.) at the dose of $5\times10^{10}$ particles per mouse. A total of sixteen mice, with four mice each vector, were used. At various points in time after vector infusion (1 week, 6 weeks), blood was collected from the animals by retro-orbital plexus bleed, and hFIX levels in the plasma were determined by hFIX ELISA (FIG. 5). Higher levels of plasma hFIX were found in mice administered AAV6 or AAV1-E531K as compared with either AAV1 or AAV6-K531E.

The foregoing is illustrative of the present invention, and is not to be construed as limiting thereof. The invention is defined by the following claims, with equivalents of the claims to be included therein.

That which is claimed is:
1. A virus vector comprising:
   (a) an adeno-associated virus (AAV) capsid comprising an amino acid substitution that results in a positively charged amino acid at amino acid position 531 in an AAV1 capsid subunit or at the corresponding amino acid position in other AAV capsid subunits; and
   (b) a recombinant nucleic acid comprising a terminal repeat (TR) sequence and a heterologous nucleic acid sequence,
wherein the recombinant nucleic acid is packaged within the AAV capsid.

2. The virus vector of claim 1, wherein said substitution is:
   (a) a substitution at amino acid position 531 of an AAV1 capsid subunit;
   (b) a substitution at amino acid position 530 of an AAV2 capsid subunit;
   (c) a substitution at amino acid position 531 of an AAV3a capsid subunit;
   (d) a substitution at amino acid position 531 of an AAV3b capsid subunit;
   (e) a substitution at amino acid position 530 of an AAV4 capsid subunit;
   (f) a substitution at amino acid position 517 of an AAV5 capsid subunit;
   (g) a substitution at amino acid position 533 of an AAV7 capsid subunit;
   (h) a substitution at amino acid position 533 of an AAV8 capsid subunit;
   (i) a substitution at amino acid position 531 of an AAV9 capsid subunit;
   (j) a substitution at amino acid position 533 of an AAV10 capsid subunit; or
   (k) a substitution at amino acid position 529 of an AAV11 capsid subunit.

3. The virus vector of claim 1, wherein said substitution is a substitution of lysine for glutamic acid at amino acid position 531 of an AAV1 capsid subunit.

4. The virus vector of claim 1, wherein said substitution is a substitution of lysine for glutamic acid at amino acid position 530 of an AAV2 capsid subunit.

5. The virus vector of claim 1, wherein said substitution is a substitution of lysine for glutamic acid at amino acid position 531 of an AAV3a or an AAV3b capsid subunit.

6. The virus vector of claim 1, wherein said substitution is a substitution of lysine for aspartic acid at amino acid position 530 of an AAV4 capsid subunit.

7. The virus vector of claim 1, wherein said substitution is a substitution of lysine for glycine at amino acid position 517 of an AAV5 capsid subunit.

8. The virus vector of claim 1, wherein said substitution is a substitution of lysine for glutamic acid at amino acid position 533 of an AAV7 capsid subunit.

9. The virus vector of claim 1, wherein said substitution is a substitution of lysine for glutamic acid at amino acid position 533 of an AAV8 capsid subunit.

10. The virus vector of claim 1, wherein said substitution is a substitution of lysine for glutamic acid at amino acid position 531 of an AAV9 capsid subunit.

11. The virus vector of claim 1, wherein said substitution is a substitution of lysine for glutamic acid at amino acid position 533 of an AAV10 capsid subunit.

12. The virus vector of claim 1, wherein said substitution is a substitution of lysine for aspartic acid at amino acid position 529 of an AAV11 capsid subunit.

13. The virus vector of claim 1, wherein the heterologous nucleic acid sequence encodes a polypeptide.

14. The virus vector of claim 13, wherein the polypeptide is a therapeutic polypeptide.

15. The virus vector of claim 14, wherein the therapeutic polypeptide is selected from the group consisting of: dystrophin, mini-dystrophin, utrophin, a clotting factor including Factor VIII or Factor IX, a growth factor including insulin-like growth factor I, insulin-like growth factor II, platelet-derived growth factor, epidermal derived growth factor, fibroblast-derived growth factor, nerve-derived growth factor, glial-derived growth factor, transforming growth factor-α or transforming growth factor-β, a neurotrophic factor, an anti-inflammatory factor including transforming growth factor-α soluble receptor or IRAP, α1-antitrypsin, lysosomal acid-α glucosidase, β-glucocerebrosidase, α-galactosidase A, a cytokine, an interferon including β-interferon, TRAIL, FAS-ligand, endostatin, angiostatin, cystic fibrosis transmembrane regulator protein, erythropoietin, LDL receptor, lipoprotein lipase, ornithine transcarbamylase, (β-globin, α-globin, spectrin, adenosine deaminase, hypoxanthine guanine phosphoribosyl transferase, sphingomyelinase, lysosomal hexosaminidase, branched-chain keto acid dehydrogenase, a bone morphogenic protein including VEGF and RANKL, protein phosphatase inhibitor I, phospholamban, serca2a, catalase, tyrosine hydroxylase, superoxide dismutase, leptin, RP65 protein, galanin, α-L-iduronidase, a hormone including insulin or somatotropin, galactocerebrosidase, phenylalanine hydroxylase, LDL receptor, soluble CD4, anti-apoptotic gene products, glutamate receptor, a lymphokine, barkct, β2-adrenergic receptor, calsarcin, enos, inos, a sarcoglycan, Fc receptor, T cell receptor, ApoE, ApoC, a suicide gene product, a tumor suppressor gene product, and any combination thereof.

16. The virus vector of claim 1, wherein the heterologous nucleic acid sequence encodes an untranslated RNA.

17. The virus vector of claim 16, wherein the untranslated RNA is an antisense RNA or an interfering RNA (RNAi).

18. The virus vector of claim 1, wherein said virus vector has enhanced binding to heparin as compared with the parent virus vector that does not contain the amino acid substitution.

19. The virus vector of claim 1, wherein the virus vector has enhanced transduction of liver as compared with the parent virus vector that does not contain the amino acid substitution.

20. The virus vector of claim 1, wherein the virus vector comprises the amino acid substitution in all of the capsid subunits.

21. A pharmaceutical formulation comprising the virus vector of claim 1 in a pharmaceutically acceptable carrier.

22. A method of delivering a nucleic acid to a cell comprising contacting the cell with the virus vector of claim 1.

23. A method of delivering a nucleic acid to a subject comprising administering to the subject the virus vector of claim 1.

24. The method of claim 23, wherein the subject is a human subject.

25. The method of claim 23, wherein the subject has or is at risk for a disorder selected from the group consisting of a muscular dystrophy including Duchenne or Becker muscular dystrophy, hemophilia A, hemophilia B, multiple sclerosis, diabetes mellitus, Gaucher disease, Fabry disease, Pompe disease, cancer, arthritis, muscle wasting, heart disease including congenital heart failure or peripheral artery disease, intimal hyperplasia, a neurological disorder including epilepsy, Huntington's disease, Parkinson's disease or Alzheimer's disease, an autoimmune disease, cystic fibrosis, thalassemia, Hurler's disease, Krabbe's disease, phenylketonuria, Batten's disease, spinal cerebral ataxia, LDL receptor deficiency, hyperammonemia, anemia, arthritis, a retinal degenerative disorder including macular degeneration, adenosine deaminase deficiency, and cancer including tumor-forming cancers.

26. A method of purifying the virus vector of claim 1 from a sample, the method comprising:
   (a) providing a solid support comprising (i) a matrix and (ii) heparin, wherein the heparin is bound to the matrix;
   (b) contacting the solid support with a sample comprising the virus vector so as to bind the virus vector to the solid support; and
   (c) eluting the bound virus vector from the solid support.

27. The method of claim 26, wherein said eluting is carried out by contacting the virus vector bound to the solid support with a high salt solution.

28. The method of claim 26, wherein said eluting is carried out by contacting the virus vector bound to the solid support with a compound that disrupts the binding of the virus vector to heparin.

29. The method of claim 28, wherein the compound is heparin, heparan sulfate, dermatan sulfate, or dextran sulfate.

30. The method of claim 28, wherein the compound is an antibody.

31. The method of claim 26, wherein the sample is a cell lysate.

32. The method of claim 26, wherein the solid support is provided in a chromatography column.

33. The method of claim 26, wherein the matrix comprises a material selected from the group consisting of fiberglass, cellulose acetate, nitrocellulose, nylon, glass, silica, alumina, ground corn grits, cellulose, agarose, polyacrylamide, or diatomaceous earth.

34. The method of claim 26, wherein the sample has been partially purified by ammonium sulfate precipitation, dialysis, size-exclusion fractionation, or density gradient fractionation.

35. A virus vector comprising:
   (a) an adeno-associated virus (AAV) capsid comprising an amino acid substitution that results in a positively charged amino acid at amino acid position 531 in an AAV1 capsid subunit or at the corresponding amino acid position in other AAV capsid subunits; and
   (b) a recombinant nucleic acid comprising a terminal repeat (TR) sequence and a heterologous nucleic acid sequence, wherein the recombinant nucleic acid is packaged within the AAV capsid; and wherein the virus vector has enhanced binding to heparin and/or heparan sulfate as compared with the parent virus vector that does not contain the amino acid substitution.

* * * * *

UNITED STATES PATENT AND TRADEMARK OFFICE
CERTIFICATE OF CORRECTION

PATENT NO. : 7,867,484 B2  
APPLICATION NO. : 11/698505  
DATED : January 11, 2011  
INVENTOR(S) : Samulski et al.

Page 1 of 1

It is certified that error appears in the above-identified patent and that said Letters Patent is hereby corrected as shown below:

In the Claims:
Column 30, Claim 15, Line 18: Please correct "(β-globin" to read -- β-globin --

Signed and Sealed this
Twenty-eighth Day of June, 2011

David J. Kappos
Director of the United States Patent and Trademark Office